United States Patent [19]
Mizuno

[11] Patent Number: 5,897,837
[45] Date of Patent: Apr. 27, 1999

[54] DISPENSING DEVICE AND IMMUNOASSAY APPARATUS USING THE SAME

[75] Inventor: Yoshiteru Mizuno, Himeji, Japan

[73] Assignee: TOA Medical Electronics Co., LTD., Hyogo, Japan

[21] Appl. No.: 08/796,546

[22] Filed: Feb. 6, 1997

[51] Int. Cl.⁶ .................................................... B01L 3/02
[52] U.S. Cl. .......................... 422/100; 422/63; 422/64; 422/65; 422/67; 436/180
[58] Field of Search ................... 422/62, 63, 64, 422/65, 67, 68.1, 100, 103; 436/179, 180

[56] References Cited

U.S. PATENT DOCUMENTS

| | | | |
|---|---|---|---|
| 3,844,661 | 10/1974 | Birkett et al. | 356/414 |
| 3,912,456 | 10/1975 | Young | 436/47 |
| 4,298,570 | 11/1981 | Lillig et al. | 422/64 |
| 4,328,185 | 5/1982 | Reasons et al. | 422/82 |
| 4,451,433 | 5/1984 | Yamashita et al. | 422/63 |
| 4,635,665 | 1/1987 | Namba et al. | 134/167 R |
| 5,260,872 | 11/1993 | Copeland et al. | 364/413.07 |
| 5,593,893 | 1/1997 | Kobashi et al. | 436/50 |

OTHER PUBLICATIONS

Duncan et al., The Boehringer Mannheim ES 300 Immunoassay System, Jounrnal of Clinical Immunoassay, vol. 14, No. 2, pp. 105–110, 1991.

*Primary Examiner*—Harold Y. Pyon

[57] ABSTRACT

A dispensing device, which may be used with an immunoassay apparatus, includes at least two dispensing pipettes for sucking and discharging liquid; a pipette elevating device for selectively raising and lowering each pipette along an elevating path thereof; a base for holding the pipette elevating device; a base moving device for moving the base; a washing vessel in which each pipette is alternately immersed to be cleaned; and a washing vessel moving device for allowing the washing vessel to selectively move between locations in the elevating paths of the pipettes.

11 Claims, 12 Drawing Sheets

DISPENSING DEVICE AND IMMUNOASSAY APPARATUS USING THE SAME

BACKGROUND OF THE INVENTION

1. Field of the Invention

The invention relates to a dispensing device, and an immunoassay apparatus using the same; and more particularly, to a dispensing device comprising a plurality of dispensing pipettes for sucking and discharging a liquid; a pipette elevating means for raising and lowering each pipette; a base to hold the pipette elevating means; a base moving means for moving the base; and a washing vessel for cleaning each pipette which can be efficiently incorporated into an immunoassay apparatus.

2. Description of the Related Art

Generally, a dispensing device is used by being incorporated in an automatic analyzing apparatus such as an immunoassay apparatus. In the dispensing device, each dispensing pipette is moved to a location over each of specimen, reagent, washing and reaction vessels, which are placed on a table of the automatic analyzing apparatus, so as to suck and discharge the specimen and the reagent to be reacted with each other followed by cleaning.

With the conventional type of dispensing device, each pipette must be moved to the washing vessel to be cleaned for the next dispensing operation each time the dispensing of the specimen or the reagent from the pipette is completed. For the automatic analyzing apparatus including this conventional type dispensing device, there has been a need for a dispensing device capable of accelerating the dispensing operation and the cleaning operation and enabling a large quantity of specimen to be analyzed with high efficiency.

SUMMARY OF THE INVENTION

An object of the invention is to provide a dispensing device enabling to accelerate dispensing steps including cleaning step and enabling a large number of specimens to be analyzed with high efficiency.

According to the invention, there is provided a dispensing device comprising at least two dispensing pipettes for sucking and discharging a liquid; a pipette elevating means for selectively raising and lowering each pipette along an elevating path thereof; a base for holding the pipette elevating means; a base moving means for moving the base; a washing vessel in which each pipette is alternately immersed to be cleaned; and a washing vessel moving means for allowing the washing vessel to selectively move between locations in the elevating paths of the pipettes.

Preferably, each dispensing pipette of the invention includes a pipette body and a fluid feeding means such as a syringe or a pump connected to the pipette body, so that the following operations can take effect in an automatic analyzing apparatus such as an immunoassay apparatus. When the pipette body is inserted in a specimen vessel or a reagent vessel, a fluid feeding means connected to the pipette body starts its sucking operation to suck up a required amount of specimen or reagent into the pipette through a piping of a flexible tube or equivalent. Then, when the pipette body is moved to and inserted into to a reaction vessel, the fluid feeding means starts its discharging operation to dispense the predetermined amount of specimen or reagent through the flexible tube. Thereafter, cleaning water or air is sucked into the pipette body and is discharged from the tip thereof. The cleaning water or air may be fed from the tip of the pipette and discharged from the pipette body. The cleaned pipette body is moved again between the next specimen and the reagent.

Preferably, the pipette elevating means comprises a pair of upper and lower horizontal axes mounted on the base; a belt stretched between the horizontal axes; a pipette moving element clamped to the belt for allowing the pipette to be held vertically; and a belt driving motor for driving the belt mounted on the base, wherein the base moving means comprises a threaded shaft including a horizontal shaft, a base moving element threadedly engaged with the threaded shaft and supporting the base, and a threaded shaft driving motor for rotating the threaded shaft.

The pipette elevating means of the invention is moved with precision in a vertical direction by drive of a belt running between pulleys or by drive of ball screw or equivalent.

Further, it is desirable that the pipette elevating means enables two or more pipettes to be selectively raised and lowered so that at least two of the pipettes alternatingly take positions at different vertical levels.

Desirably, the pipette elevating means is adapted so that a pipette stopping position is preset for each pipette to be stopped when it is lowered into the washing vessel located in the corresponding pipette elevating path.

Also, it is desirable that the pipette stopping position is so preset that the tip of the pipette may not be brought into contact with and damaged by the washing vessel, but the tip portion of the pipette contaminated by the specimen or reagent is immersed in the cleaning liquid in the washing vessel. It is preferable for simplification of control to set each pipette stopping position to have the same vertical level. The presetting of each pipette stopping position may be made arbitrarily depending on their vertical levels at which the pipettes perform the dispensing. The pipette stopping positions may alternatively be determined by a liquid level sensor. An example of the liquid level sensor is one which is used in a washing vessel formed of a dielectric and includes a sensor for sensing a change in capacitance between the washing vessel and the pipette when the tip of the pipette is brought into contact with the liquid in the washing vessel.

Preferably, the base moving means is moved with precision in a horizontal direction by drive of a belt running between pulleys or by drive of ball screw or equivalent.

Further, it is desirable that the base moving means is capable of being linked, in operation, with at least one of the washing vessel moving means, the pipette elevating means, the washing vessel cleaning means, and the fluid feeding means. The washing vessel moving means, the washing vessel cleaning means and the fluid feeding means will be described later.

Preferably, the washing vessel of the invention has a height and a cross section sufficient to receive at least a tip portion of the pipette so that the vessel can contain a predetermined amount of cleaning liquid to rinse the specimen or the reagent adhering to the pipette therefrom. At least one washing vessel is arranged on the base. It is desirable that the washing vessel is formed to receive one pipette body at a time. Alternatively, the washing vessel may be adapted to receive two or more pipette bodies, e.g., a set of pipette bodies arranged in parallel with each other to be raised and lowered simultaneously.

The washing vessel moving means of the invention is formed by an actuator which allows the washing vessel to orderly rotate, swing, or linearly move between locations in the elevating paths of the pipettes defining a starting point and an endpoint of such a movement of the washing vessel. The washing vessel moving means of the invention includes a means to allow the arms holding the washing vessel to be rotated in forward and backward directions or reciprocated linearly by the actuator or equivalent.

Further, it is preferable that the washing vessel moving means is in the form of an actuator which, when a first pipette is in its lower position, allows the washing vessel to be positioned in place in the elevating path of a second pipette which is in its upper position, and, when the second pipette is in its lower position, allows the washing vessel to be positioned in place in the elevating path of the first pipette which is now in its upper position. Desirably, the washing vessel is connected to a washing vessel cleaning means for introducing a cleaning liquid in and out of the washing vessel, and the pipettes are connected to a fluid feeding means for supplying a cleaning fluid into the pipettes.

Additionally, it is advantageous that the washing vessel moving means comprises (i) a rotary actuator mounted on the base and having a vertical rotary axis and (ii) an arm having one end supported by the vertical rotary axis and the other end supporting the washing vessel.

Preferably, the washing vessel cleaning means comprises a liquid feeding path connected to a lower part of the washing vessel, a liquid discharging path connected to an upper part of the washing vessel, and a washing vessel pump which is connected to the liquid feeding path so that the cleaning liquid can be fed from the lower part of the washing vessel and discharged from the upper part of the washing vessel through the liquid discharging path, wherein the fluid feeding means comprises a quantifying syringe connected to an upper end portion of the pipette and a pipette pump capable of feeding the cleaning liquid to the quantifying syringe.

Preferably, the dispensing device further comprises a vessel sensing means for sensing the washing vessel positioned in place in either of the elevating paths of the pipettes.

Advantageously, the vessel sensing means includes a controlling section to which a magnetic sensor, a micro switch and the like are connected, so that the controlling section can command to clean the pipette when the vessel sensing means senses the washing vessel positioned in place in either of the elevating paths of the pipettes.

Further, the vessel sensing means preferably comprises a magnet fixed to the arm and Hall effect devices which are located in such places in the pipette elevating paths as to be linked in operation with the magnet.

DETAILED DESCRIPTION OF PREFERRED EMBODIMENT

Figure 1:
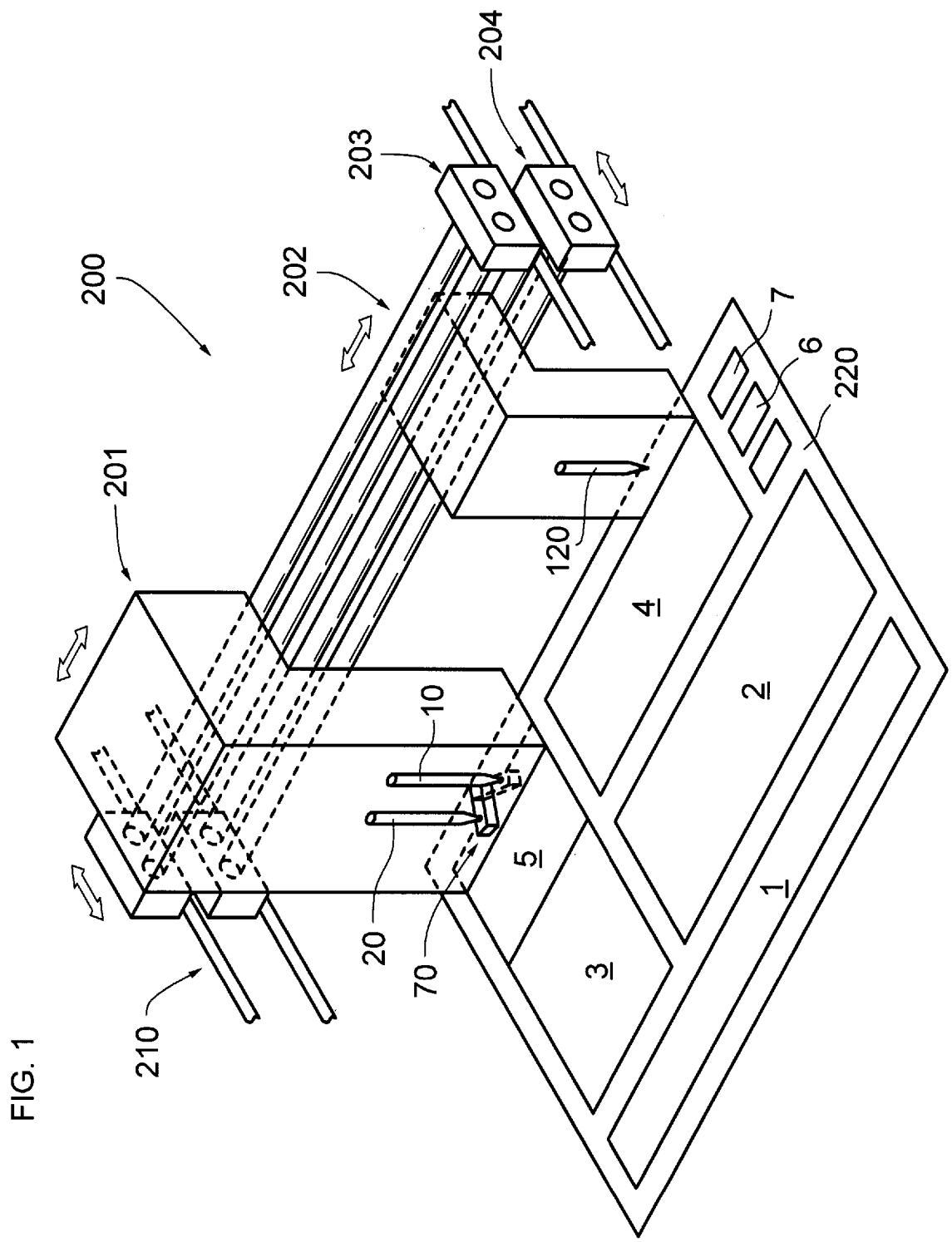
FIG. 1 is a schematic diagram of an automatic analyzing apparatus (an immunoassay apparatus) including a dispensing device according to one embodiment of the invention.

One example of an apparatus using the dispensing device of the invention is an immunoassay apparatus comprising a table on which specimens including blood, reagents, and reaction vessels are placed; an immunoassay section; a specimen/reagent dispensing section disposed above the table for dispensing the specimen and the reagent into the reaction vessels; and a reacted solution dispensing section for dispensing reacted solutions from the reaction vessels to said measuring section, wherein said specimen/reagent dispensing section is formed by the dispensing device of the invention.

Next, operation of the dispensing device of the invention, applied to an immunoassay apparatus, will be described below. In this example, one of the pipettes is used as a pipette for use in dispensing a specimen (hereinafter referred to as a specimen pipette) and the other is used as a pipette for use in dispensing a reagent (hereinafter referred to as a reagent pipette), for minimization of contamination.

First, the base is moved to a selected specimen by the drive of the base moving means. The specimen pipette, ready for use, is lowered by the pipette elevating means and the tip portion of the same is immersed into the specimen including blood to suck up a required amount of specimen. Then, the base is moved to a selected reaction vessel and the specimen sucked up in the pipette is ejected from the pipette into the reaction vessel. After completion of the ejection, the specimen pipette is raised by the pipette elevating means to be on standby for the next operation.

During this dispensing process of the specimen pipette, the reagent pipette held together with the specimen pipette on the base is in the cleaning process. In the cleaning process, the reagent pipette is immersed into the washing vessel positioned in place in the elevating path of the reagent pipette and is cleaned. After completion of the cleaning, the reagent pipette is raised from the washing vessel by the pipette elevating means. When the reagent pipette is raised to be on standby, the washing vessel is shifted to a location in the elevating path of the specimen pipette by the washing vessel moving means.

Then, the base is moved to the reagent by the drive of the base moving means. The reagent pipette, ready for use, is lowered by the pipette elevating means and the tip portion of the same is immersed into the reagent to suck up a required amount of reagent. Then, the base is moved to the reaction vessel and the reagent sucked up in the pipette is ejected from the pipette into the reaction vessel. After completion of the ejection, the reagent pipette is raised by the pipette elevating means to be on standby for the next operation.

During this dispensing process of the reagent pipette, the specimen pipette held together with the reagent pipette on the base is in the cleaning process. In the cleaning process, the specimen pipette is immersed into the washing vessel positioned in place in the elevating path of the specimen pipette and is cleaned. After completion of the cleaning, the specimen pipette is raised by the pipette elevating means. When the specimen pipette is raised to be on standby, the washing vessel located in the elevating path of the specimen pipette is shifted from the location in the elevating path of the specimen pipette to the location in the elevating path of the reagent pipette by the washing vessel moving means to be on standby for the next operation.

This constitution of the invention can provide the result that the process of reciprocating the pipettes used for the dispensing to the washing vessel fixed on the table every time, which is required in the conventional dispensing device, is omitted. Also, in tandem with the discharging action of one pipette or the moving action of the base, the other pipette can be cleaned simultaneously. Consequently, the dispensing of specimen or reagent can be continuously carried out without being retarded by the cleaning.

Where the washing vessel moving means is in the form of an actuator which, when one of the pipettes is in its lower position, allows the washing vessel to be positioned in place in the elevating path of the other pipette which is in its upper position, and, when the other pipette is in its lower position, allows the washing vessel to be positioned in place in the elevating path of the one pipette which is in its upper position, it can be ensured that each pipette is not hindered from its lowering motion by the washing vessel when it is lowered to the dispensing position.

Where the washing vessel is connected to a washing vessel cleaning means for introducing a cleaning liquid in and out of the washing vessel, and the pipettes are connected to a fluid feeding means for supplying a cleaning liquid into the pipettes, both the exterior and the interior of each pipette immersed in the washing vessel can be cleaned by use of the washing vessel cleaning means and the fluid feeding means, respectively.

Further, where the base moving means is capable of being linked, in operation, with at least one of the washing vessel moving means, the pipette elevating means, the washing vessel cleaning means, and the fluid feeding means, that can provide the result that at least a part of the cleaning process is performed simultaneously while one of the pipettes held on the base is moved.

Additionally, where the washing vessel moving means comprises a rotary actuator mounted on the base and having a vertical rotary axis and an arm having one end supported by the vertical rotary axis and the other end supporting the washing vessel, that can provide the result that the arm is simply required to swing or pivot around the vertical rotary axis of the rotary actuator to move between the two places. Consequently, the control of the washing vessel moving means can be facilitated.

Also, where the dispensing device further comprises a vessel sensing means for sensing the washing vessel positioned in place in one of the elevating paths of the pipettes, it can be ensured that the pipettes are prevented from being damaged and also the tip portions of the pipettes are introduced into the washing vessel.

Further, where the pipette elevating means is adapted so that a pipette stopping position is preset for each pipette to be stopped when it is lowered into the washing vessel located in the corresponding pipette elevating path, it can be ensured that the tip portion of the pipette is protected against being brought into contact with and damaged by the washing vessel and also it can be ensured that the tip portion of the pipette with the specimen or reagent adhering thereto is immersed in the cleaning liquid in the washing vessel.

A better understanding of the invention may be provided by referring to the accompanying drawings. FIG. 1 shows an example of an automatic immunoassay apparatus equipped with a dispensing device of an embodiment of the present invention. The basic configuration of the apparatus, including system of reaction, system of measurement and the like, is the same as the known ones. The automatic immunoassay apparatus 200 is constructed mainly of a dispensing device 210 and a table 220 on which a specimen, a reagent and equivalent are to be positioned.

The dispensing device 210 comprises the first dispensing block 201 having two pipettes of the invention, the second dispensing block 202 having one pipette, the first block moving means 203 and the second block moving means 204 which form a base moving means for moving the first and second blocks 201,202 along X and Y axes.

Figure 2:
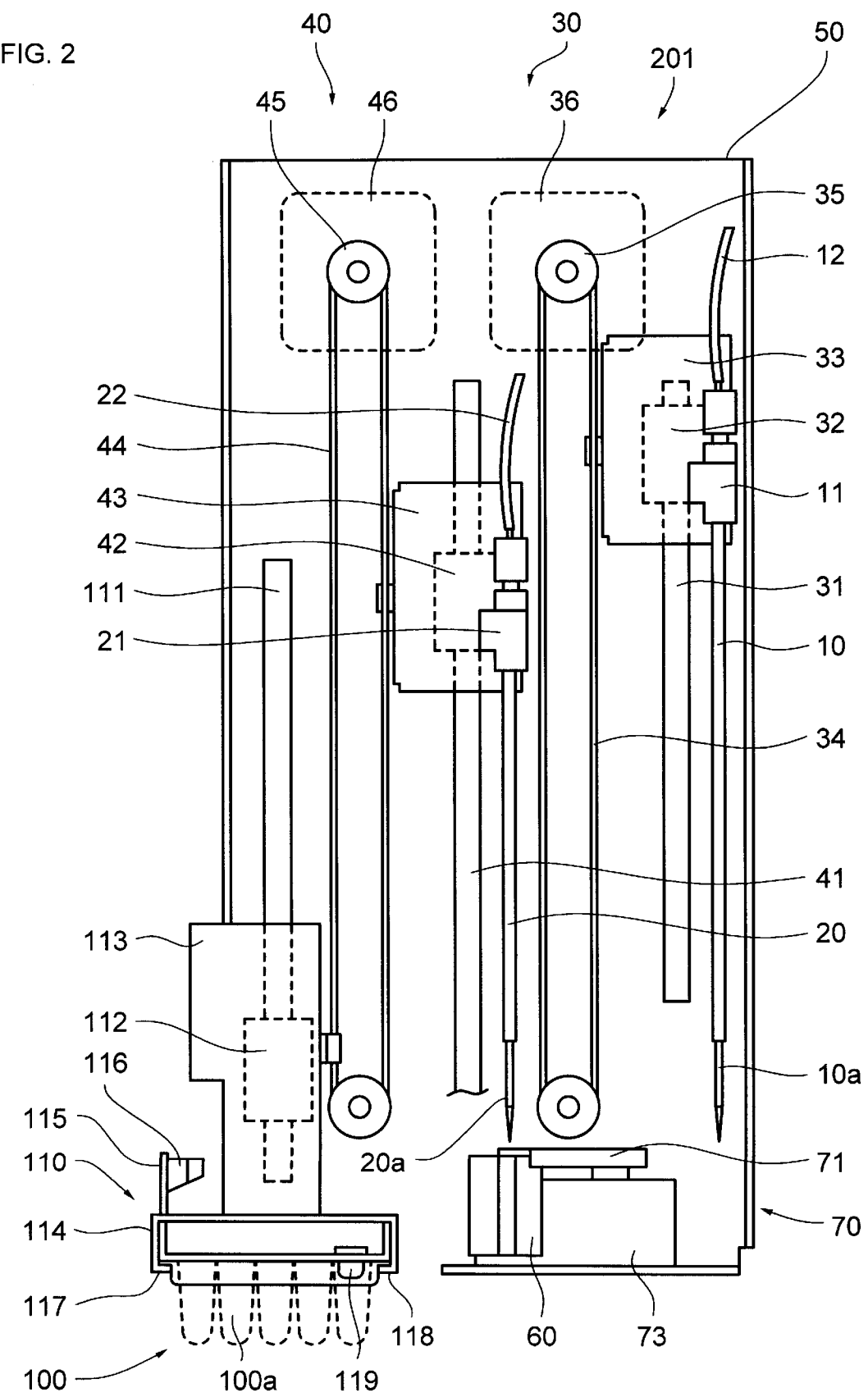
FIG. 2 is a view of the dispensing device of FIG. 1 (showing the pipette on standby)

The first dispensing block 201 is constructed mainly of two dispensing pipettes 10, 20, pipette elevating means 30, 40 for elevating the respective pipettes 10, 20, and a base 50 holding the pipettes 10, 20 and the pipette elevating means 30, 40, as shown in FIG. 2.

Figure 3:
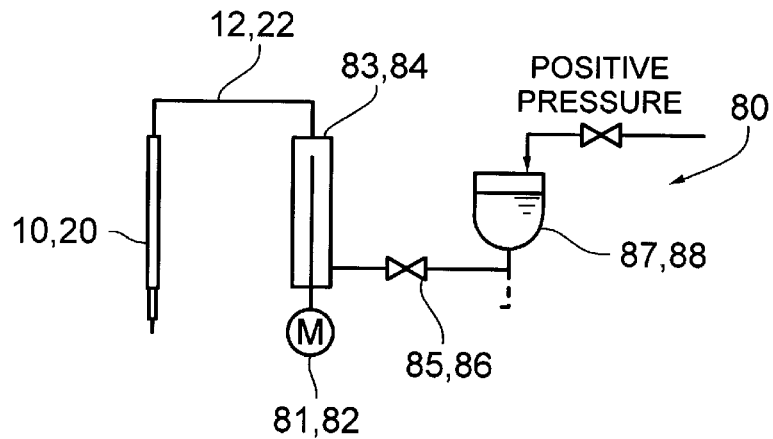
FIG. 3 is a view of a pipette liquid feeding means of the dispensing device of FIG. 2.

The dispensing pipettes 10, 20 are attached at the upper end portions thereof to connecting pipes 11, 21 so as to be hung therefrom. Tubes 12, 22 communicating with the pipettes 10, 20 are coupled to the connecting pipes 11, 21. The respective tubes 12, 22 are connected to a pipette liquid feeding means 80, as shown in FIG. 3. The pipette liquid feeding means 80 is connected to syringes 83, 84 driven by motors 81, 82. The syringes 83, 84 are connected to cleaning liquid chambers 87, 88 from which the cleaning liquid supplied by positive pressure from the outside is fed toward the syringes 83, 84 through solenoid valves 85, 86. This pipette liquid feeding means 80 allows the dispensing of the specimen or the reagent and the cleaning of the interior of the pipettes 10, 20 to be performed by switching of the solenoid valves 85, 86. The connecting pipes 11, 21 are mounted on the pipette elevating means 30, 40.

The pipette elevating means 30, 40 comprise vertically extending guide tracks 31, 41 fixed to the base 50; sliders 32, 42 movable up and down along the guide tracks 31, 41; belts 34, 44 on which the sliders 32, 42 are fixedly mounted via mounting members 33, 43; a pair of pulleys 35, 45 between which the belts 34, 44 are stretched in a vertical direction; and motors 36, 46 for rotatively driving one of the pulleys 35, 45.

The elevating means 30, 40 allow the specimen pipette 10 and the reagent pipette 20 to be raised and lowered by the forward and backward rotations of the motors 36, 46. The pipettes 10,20 are each stopped at their standby position (an upper position), at their stopping position at which a tip portion 10a, 20a of each of the pipettes 10, 20 entering a washing vessel 60 mentioned later is stopped and at their dispensing position (a lower position), respectively. At the bottom of the base 50 under the pipettes 10, 20, there are provided a washing vessel 60 and a washing vessel moving means 70 for moving the washing vessel 60 horizontally, as shown in FIG. 4.

Figure 4:
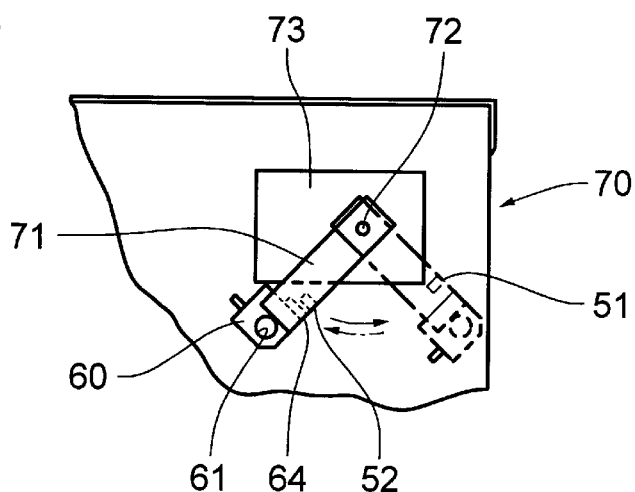
FIG. 4 is a plan view of a washing vessel moving means located in a part of the dispensing device of FIG. 2.
Figure 5:
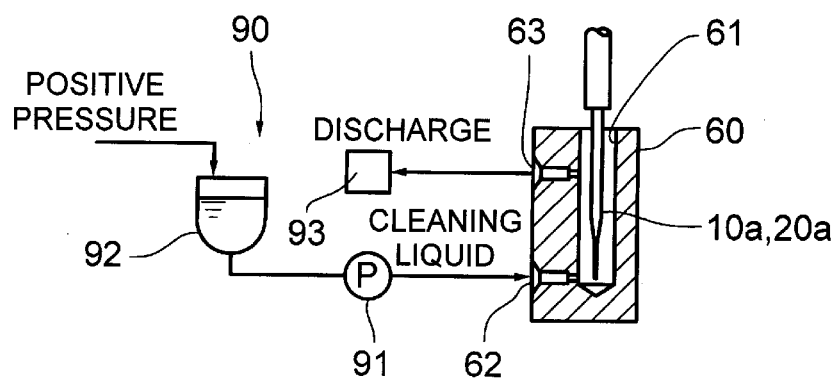
FIG. 5 is a view showing the sectional view of the washing vessel disposed in a washing vessel moving means of FIG. 4 and illustrating the washing vessel liquid feeding means.

The washing vessel 60 is provided with a hole 61 for the tip portion 10a, 20a of each of the pipettes 10, 20 to enter, a cleaning liquid inlet 62 and a cleaning liquid outlet 63 both communication with the hole 61, as shown in FIGS. 4 and 5. To the cleaning liquid inlet 62 and the cleaning liquid outlet 63 is connected a cleaning liquid feeding means 90 as shown in FIG. 5. The cleaning liquid feeding means 90 comprises a pump 91 and a cleaning liquid chamber 92 connected to the pump 91 and enables the cleaning liquid stored in the hole 61 of the washing vessel 60 to be replaced at appropriate times. The cleaning liquid outlet 63 is connected to a discharge liquid reservoir 93. A magnet 64, which forms a washing vessel sensing means mentioned later, is provided on an outer wall of the washing vessel 60.

The washing vessel moving means 70 comprises an arm 71 holding the washing vessel 60 at the one end thereof and a driving means 73 including a rotary actuator capable of reciprocally pivoting around a pivot shaft 72 provided at the other end of the arm 71. The pivotal motion of the arm 71 is controlled via a controlling section not shown by use of the magnet 64 provided on the washing vessel 60 and Hall effect devices 51, 52 provided on a bottom of the base 50.

The Hall effect devices 51, 52 are spaced apart from each other in such a manner that when the hole 61 of the washing vessel 60 is positioned in place in the elevating path of the specimen pipette 10, the Hall effect device 51 confronts the magnet 64 in proximity thereto, while on the other hand, when the opening 61 of the washing vessel 60 is positioned in place in the elevating path of the reagent pipette 20, the Hall effect device 52 confronts the magnet 64 in proximity thereto. When the magnet 64 at the arm 71 swinging in a counterclockwise direction (in a direction indicated by an arrow depicted in a solid line in FIG. 4) is brought into the proximity of the Hall effect device 51 by the driving means 73 driven in the forward direction, the swinging motion of the arm 71 caused by the driving means 73 is stopped, so that the hole 61 of the washing vessel 60 is positioned in place in the elevating path of the specimen pipette 10. When a command to switch the position of the washing vessel 60 is issued from the controlling section, the rotation of the driving means 73 is reversed to allow the arm 71 to swing in a clockwise direction (in a direction indicated by an arrow depicted in a chain line in FIG. 4).

When the magnet 64 at the arm 71 swinging in the clockwise direction is brought into the proximity of the Hall effect device 52, the swinging motion of the arm 71 caused by the driving means 73 is stopped, so that the hole 61 of the washing vessel 60 is positioned in place in the elevating path of the reagent pipette 20. When a command to switch the position of the washing vessel 60 is issued from the controlling section, the driving means 73 is driven in the forward direction again, so that the hole 61 of the washing vessel 60 is positioned in place in the elevating path of the specimen pipette 10. In this manner, the washing vessel moving means 70 allows the washing vessel 60 to be selectively positioned in place in each of the elevating paths of the pipettes 10 and 20. Thus, the washing vessel moving means 70 interlocking in operation with the aforesaid pipette elevating means 30, 40 enables the two pipettes 10, 20 to be alternately cleaned at their pipette stopping positions with the single washing vessel 60.

There is provided a reaction vessel holding means 110 at the rear of the belt 44 to which the reagent pipette 20 is disposed. The reaction vessel holding means 110 is attached via an attachment 113 to a slider 112 movable up and down along a guide track 111 mounted to the base 50 in parallel with said guide track 31. The holding means 110 includes a mounting member 114 having a U-like shape with the front ends thereof folded inside, in other words, with a center part of a bottom side of rectangle cut out. The mounting member 114 is provided with a vertical member 115 and a positioning sensor 116 fixed to the vertical member 115.

Figure 6:
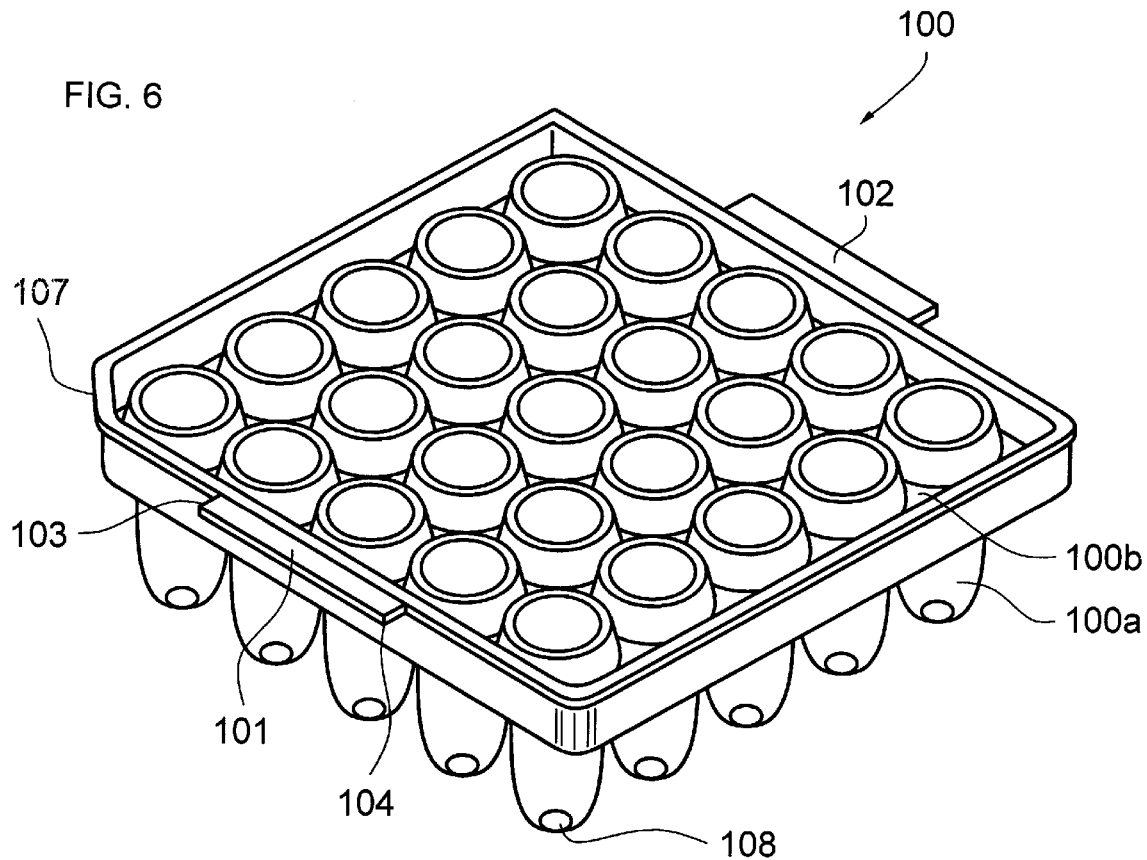
FIG. 6 is a perspective view of a reaction plate held by a reaction vessel holding means of the dispensing device of FIG. 2.

The mounting member 114 is provided at the front ends thereof with bent portions 117, 118 to which handles 101, 102 of a reaction plate 100 is fitted for holding the reaction plate 100. Handle 101 of the reaction plate 100 is provided at both lower ends thereof with holding projections 103, 104, as shown in FIG. 6. The holding projections 103, 104 are so located as to catch the bent portion 117 from the outside, so that the reaction plate 100 is held in place and does not move out of position, when being lifted up.

Further, a cylindrical member 119 having a rounded top is provided in the base 50. The cylindrical member 119 is fitted into a reaction vessel 100a of the reaction plate 100 when the reaction plate 100 is lifted up by the holding means 110. Thus, the reaction plate 100 is firmly held without moving out of position by the longitudinal or transverse movement.

The reaction plate 100 is an integrally-molded transparent plate of synthetic resin. Each reaction plate has, for example, 25 reaction vessels 100a having 5 vessels on each side (5×5) and is integrally formed of synthetic resin in such a manner that the vessels 100a are adjoined to each other through a base plate 100b. Each vessel 100a has an internal diameter of for example about 8 mm and a height of for example about 24 mm. The reaction plate 100 is substantially square in shape, about 70 mm on each side, for example, when viewed from the above.

An upper end and a lip portion of each reaction vessel 100a is located higher than the base plate 100b (by 6 mm in this embodiment), so that a liquid in the reaction vessel 100a seldom spills out and also a liquid spilt over the base plate 100b seldom enters the vessel 100a. The reaction plate 100 is partially cut out at a corner 107 for the positioning thereof. Each vessel 100a is provided at its bottom with a recess 108, which contributes to unfluctuated dimension in production and ensures a stable mounting to the apparatus.

With this construction, according as the holding means 110 is lowered by the drive of the pipette elevating means 40 for holding or releasing the reaction plate 100, the pipette 20 is raised and thus does not hinder the holding means from holding or releasing the reaction plate 100. Likewise, according as the pipette 20 is lowered, the holding means 110 is raised and thus does not hinder the pipette 20 from the dispensing operation.

Figure 7:
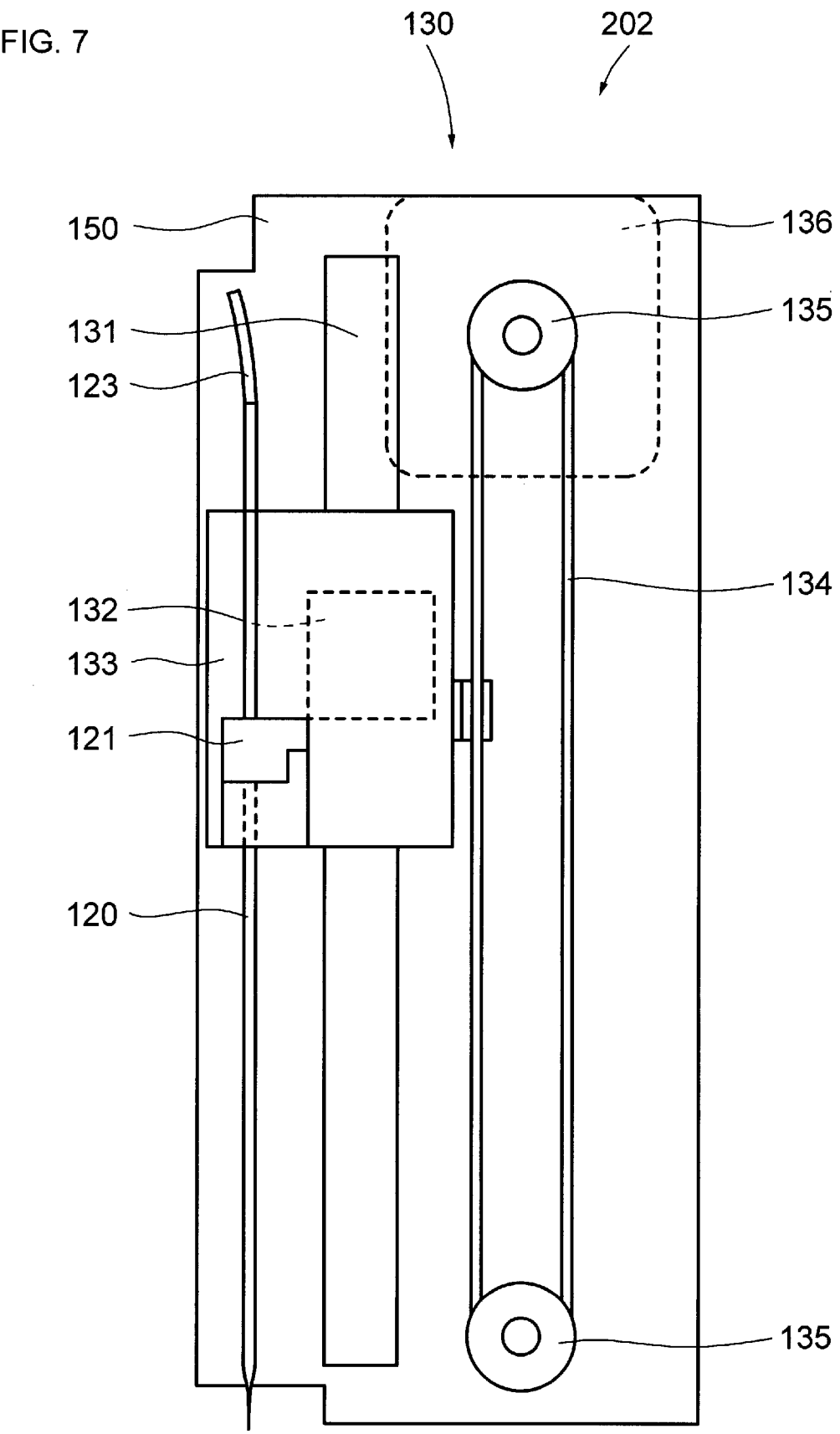
FIG. 7 is a view of the second dispensing block disposed in the automatic analyzing apparatus of FIG. 1.

The second dispensing block 202 is constituted mainly of one pipette 120 for use in dispensing of a reacted solution (hereinafter referred to as a reacted solution pipette), a pipette elevating means 130 for raising and lowering the reacted solution pipette 120, and a base 150 holding the pipette 120 and the elevating means 130, as shown in FIG. 7.

The reacted solution pipette 120 is attached at its upper end portion to a connecting pipe 121 so as to be hung therefrom. A tube 123 communicating with the pipette 120 is coupled to the connecting pipe 121. The tube 123 is connected to a pipette liquid feeding means 80 equivalent to the one shown in FIG. 3 so that an interior of the pipette 120 can be cleaned. The connecting pipe 121 is mounted to the pipette elevating means 130.

Like the abovesaid pipette elevating means 30, the pipette elevating means 130 comprises a vertically extending guide track 131 fixed to the base 150; a slider 132 movable up and down along the guide track 131; a belt 134 to which the slider 132 is fixedly mounted via a mounting member 133; a pair of pulleys 135 between which the belt 134 is stretched in a vertical direction; and a motor 136 for rotatively driving one of the pulleys 135.

The elevating means 130 allows the reacted solution pipette 120 to be raised and lowered by forward and backward rotations of the motor 136. Nothing corresponding to the washing vessel 60 and the washing vessel moving means 70 included in the first dispensing block 201 is mounted on the base 150.

A table 220 is provided under the dispensing device 210 (See FIG. 1). An upper surface of the table 220 is partitioned into a specimen placing section 1 where a specimen rack is placed, a reagent placing section 2 where a reagent rack is placed, an empty vessel placing section 3 where an empty reaction vessel is placed, a reaction vessel placing section 4 where a vessel containing reacted solution is placed, a used vessel placing section 5 where a used reaction vessel is placed, a measurement introducing section 6 for introducing a reacted solution into system of measurement, and a pipette cleaning section 7. These sections are all arranged in one plane.

Figure 8:
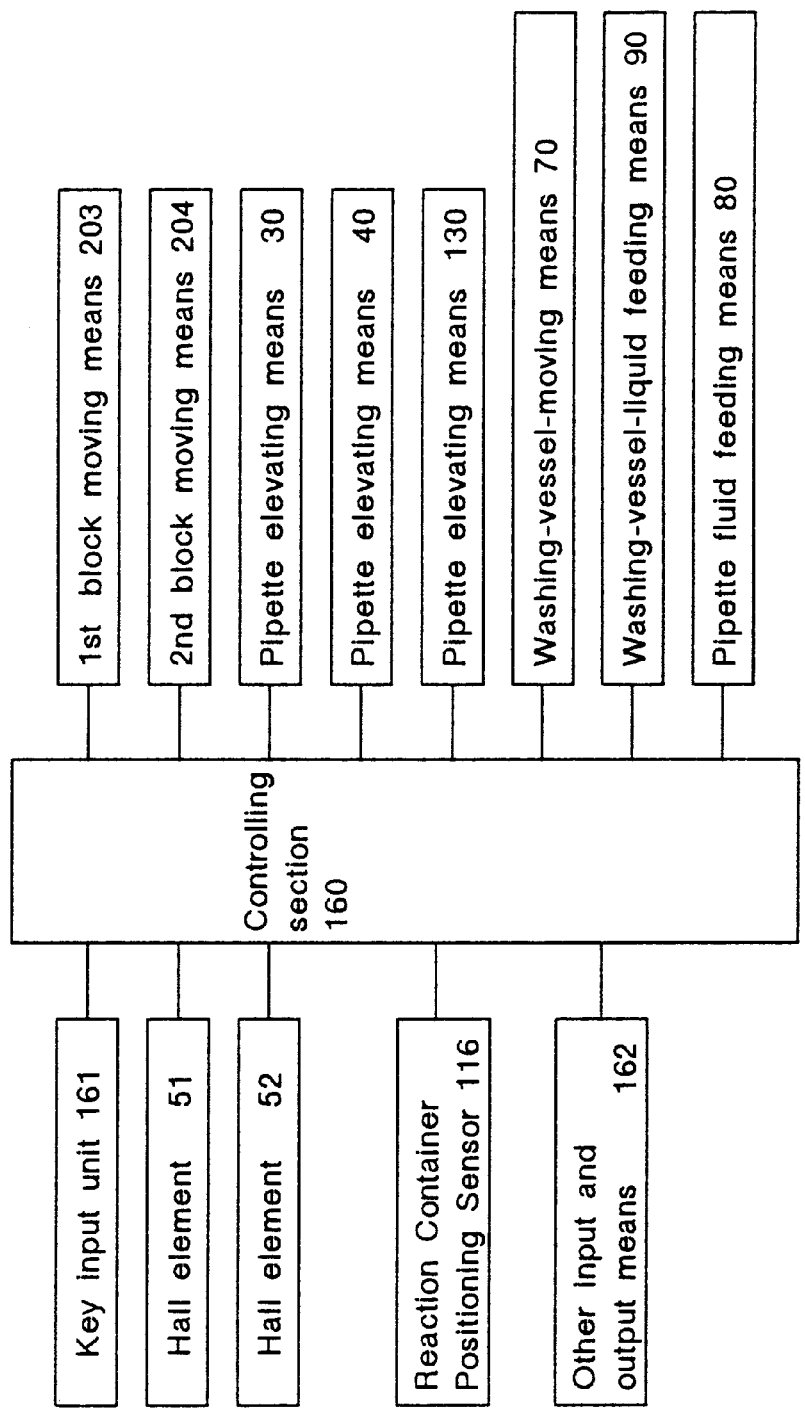
FIG. 8 is a block diagram of a controlling section of the automatic analyzing apparatus of FIG. 1.
Figure 9:
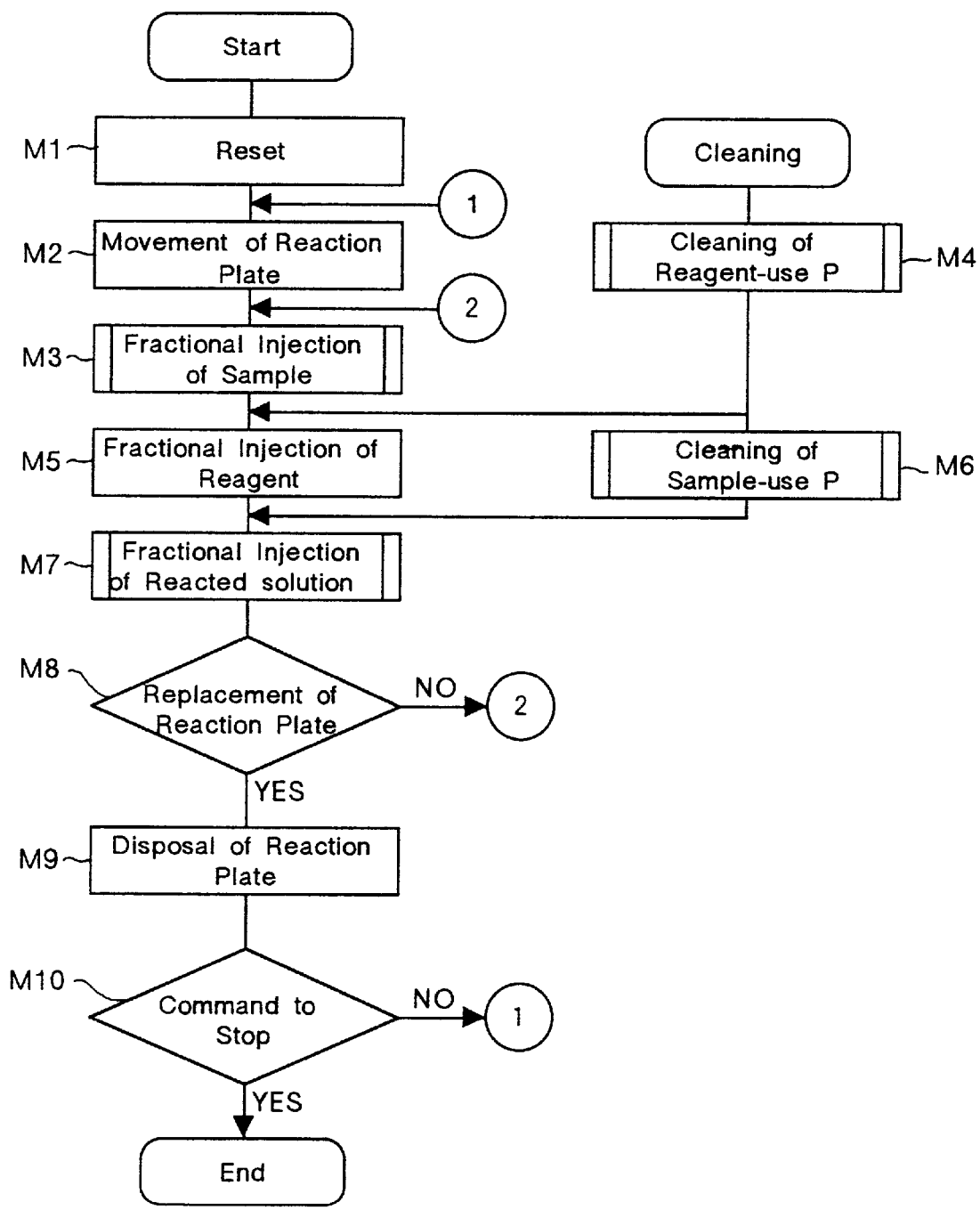
FIG. 9 is a flowchart of the control of the automatic analyzing apparatus of FIG. 1.
Figure 10:
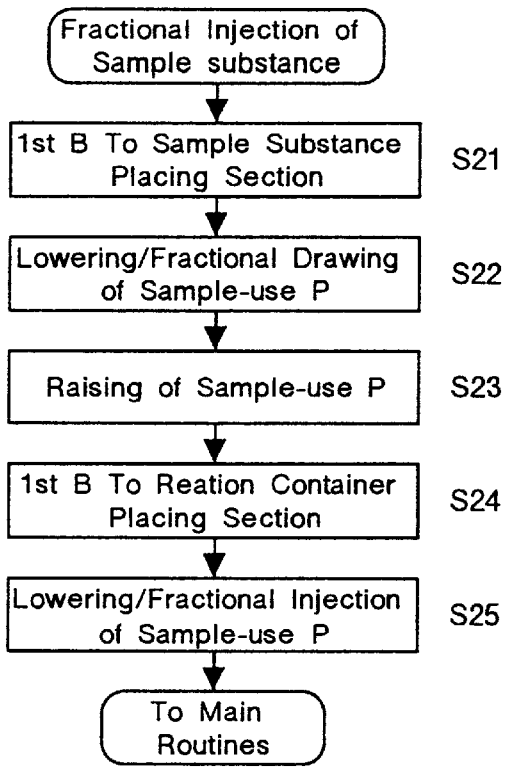
FIG. 10 is a flowchart of the dispensing of the specimen of FIG. 9.
Figure 11:
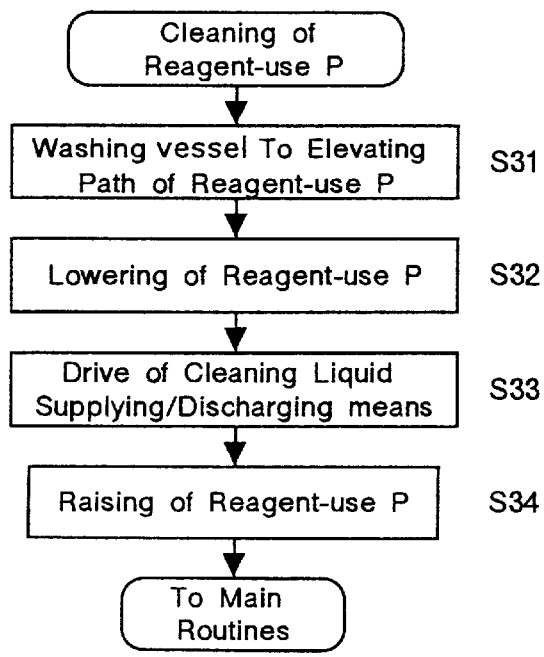
FIG. 11 is a flowchart of the cleaning of a reagent pipette of FIG. 9.
Figure 12:
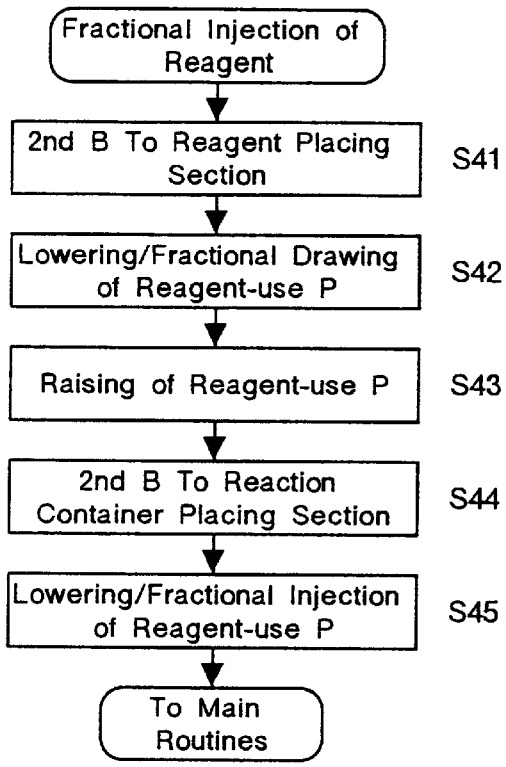
FIG. 12 is a flowchart of the dispensing of a reagent in FIG. 9.
Figure 13:
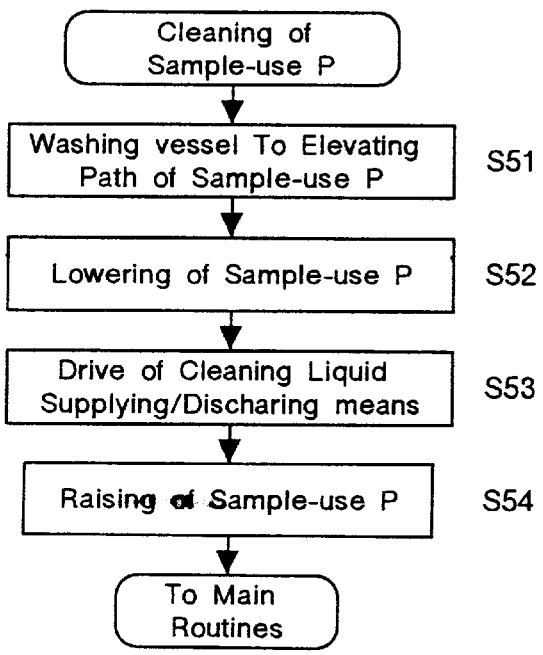
FIG. 13 is a flowchart of the cleaning of the specimen pipette of FIG. 9.
Figure 14:
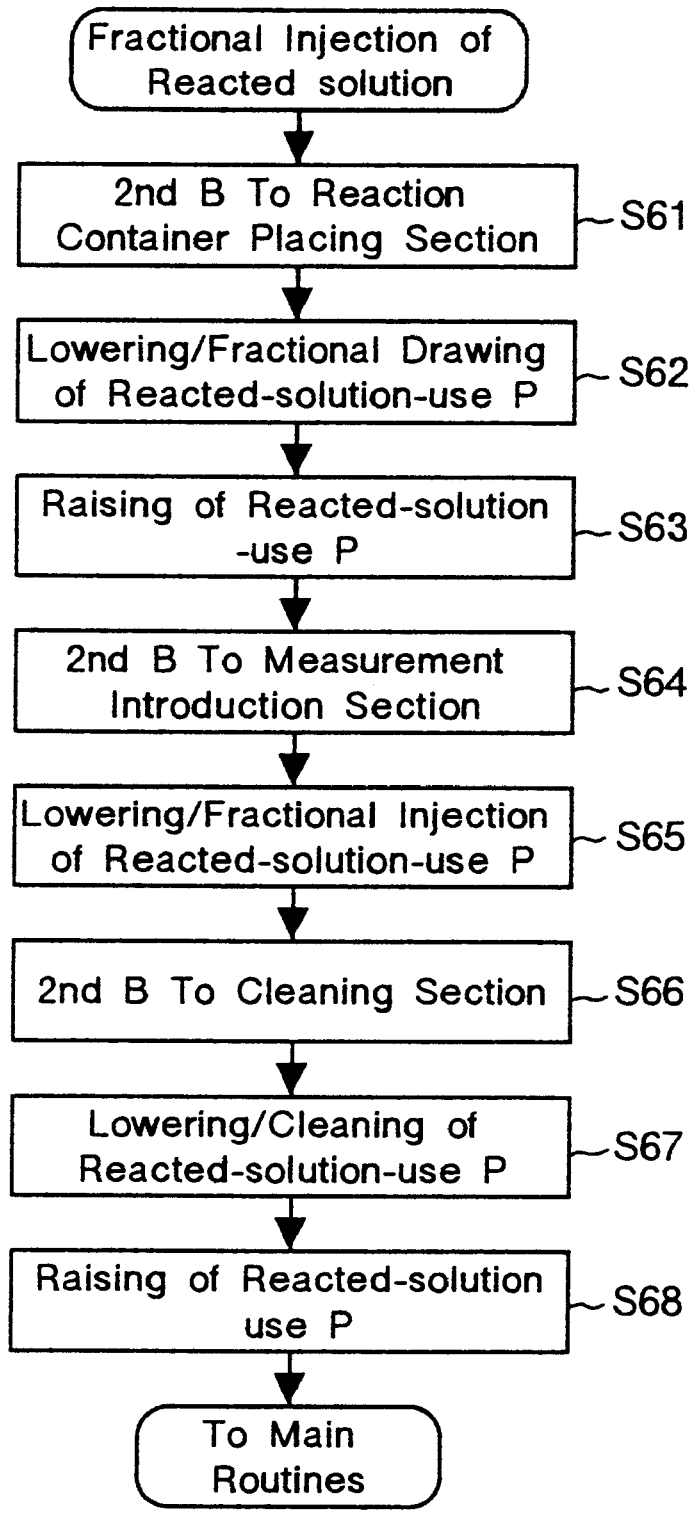
FIG. 14 is a flowchart of the dispensing of a reacted solution in FIG. 9.

Further, the input and output sections mentioned above are electrically connected to a controlling section mentioned later. FIG. 8 is a block diagram of an immunoassay apparatus 200.

The immunoassay apparatus 200 has the controlling section 160 including a microcomputer comprising CPU, ROM, RAM, a timer, a counter, and the like. The input section, including an external key input unit 161 (not shown), the Hall effect devices 51, 52, and the reaction vessel positioning sensor 116, is connected to the controlling section 160. Also, the output section, including block moving means 203, 204, the pipette elevating means 30, 40, 130, the washing vessel moving means 70, the washing vessel liquid feeding means 90 and the pipette liquid feeding means 80, is connected to the controlling section 160 together with other input and output section 162.

Next, with reference to the flowcharts of FIGS. 9 to 14, operation of the immunoassay apparatus 200 of the embodiment will be described below.

First, the input and output sections are reset at step M1. Second, the reaction plate 100 is moved at step M2, at which the first dispensing block 201 is moved by the drive of the first block movable means 203 to a location over the empty vessel placing section 3 and then the holding means 110 is lowered by the drive of the pipette elevating means 40 to hold the reaction plate 100. After holding the reaction plate 100, the holding means is raised and is moved to a location over the reaction vessel placing section 4. Then, the holding means 110 is lowered to put the reaction plate 100 in place on the reaction vessel placing section 4.

Then, the dispensing of the specimen is performed at step M3. In detail, the dispensing of the specimen is performed in the order shown by the subroutines of FIG. 10: First, at step S21 the first dispensing block 201 is moved to a location over the specimen placing section 1 and is stopped at a location over a selected specimen rack. Then, at step S22 the tip portion of the specimen pipette 10 is lowered into the selected specimen rack, so as to suck up the specimen.

After the specimen pipette 10 is raised and stopped at step S23, the first dispensing block 201 is moved to a location over the reaction vessel placing section 4 and then the specimen pipette 10 is stopped at a location over a selected reaction vessel 100a on the reaction plate 100 at step S24. Then, at step S25 the tip portion of the specimen pipette 10 is lowered into the selected reaction vessel 100a so as to dispense the specimen thereinto. During this process, the washing vessel 60 remains on the reagent pipette 20 side. After completion of the dispensing of the specimen, the specimen pipette 10 is raised to be on standby for the next operation.

Figure 15:
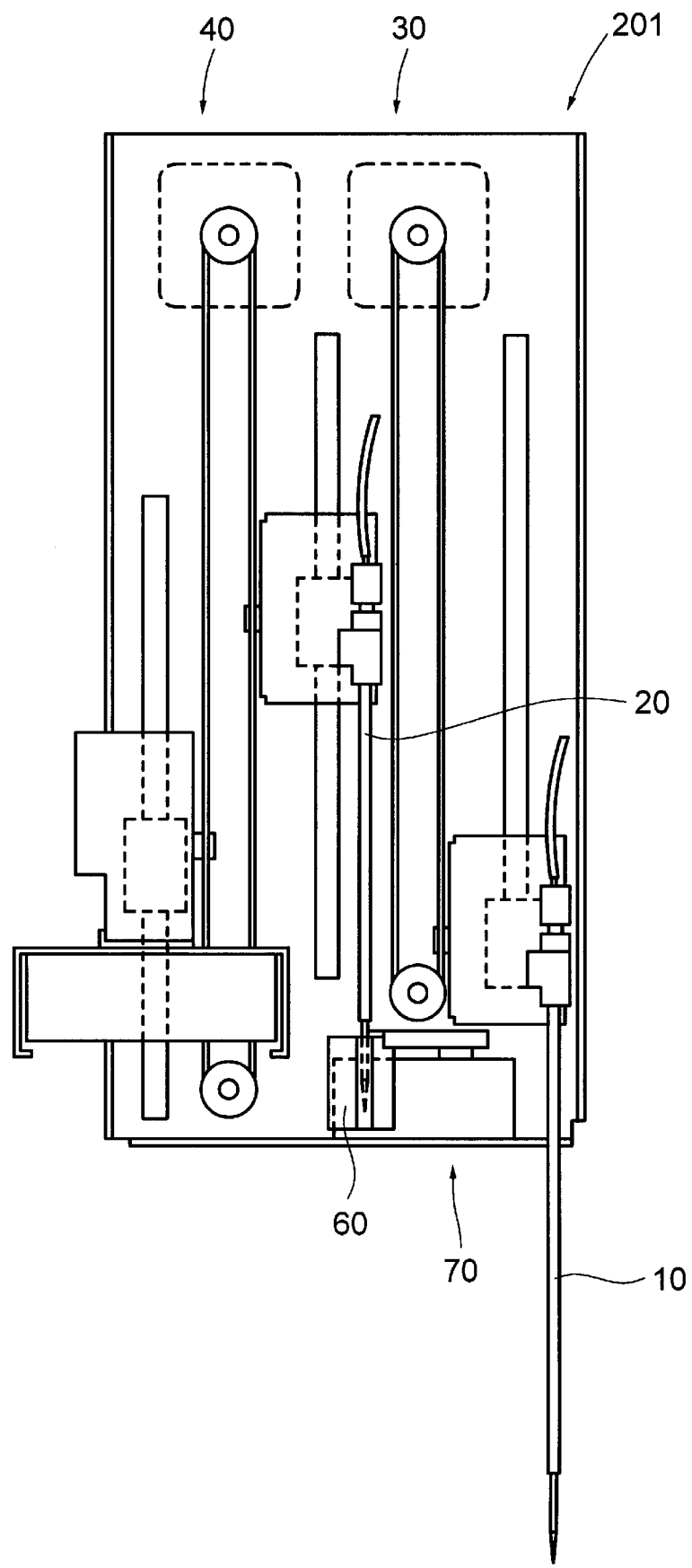
FIG. 15 is a view corresponding to FIG. 2, illustrating the cleaning operation of the reagent pipette and the position of the washing vessel moving means at the time of the dispensing with the specimen pipette.

During this process, the reagent pipette 20 is in the cleaning process at step M4. In detail, the cleaning process of the reagent pipette 20 is performed in the order shown by the subroutines of FIG. 11: First, the washing vessel 60 is positioned in place in the elevating path of the reagent pipette 20 at step S31. The hole 61 of the washing vessel 60 is supplied in advance with a cleaning liquid. Then, at step S32 the tip portion of the reagent pipette 20 is lowered into the washing vessel 60 and is stopped at its pipette stopping position, as shown in FIG. 15.

At step S33 the closing and opening of the solenoid valve 86 connected to the reagent pipette 20 and the drive of the motor 82 allow the cleaning liquid from the pipette liquid feeding means 80 to flow into the reagent pipette 20 through the syringe 84, so as to clean the interior of the pipette 20. Further, the cleaning liquid is additionally supplied to the washing vessel 60 from the cleaning liquid chamber 92 of the washing vessel liquid feeding means 90. The additional cleaning liquid fed from the cleaning liquid inlet 62 forces the wasted cleaning liquid in the washing vessel 60 to be discharged from the cleaning liquid outlet 63, cleaning simultaneously the exterior of the reagent pipette 20 at the tip portion.

After completion of the cleaning, the reagent pipette 20 situated in the washing vessel 60 is raised by the pipette elevating means 40 at step S43. When the pipette 20 is raised to be on standby for the next operation, the washing vessel 60 located in the elevating path of the reagent pipette 20 is shifted to a place in the elevating path of the specimen pipette 10 by the washing vessel moving means 70.

After completion of the dispensing of the specimen at step M3, the dispensing of the reagent is performed at step M5. In detail, the dispensing of the reagent is performed in the order shown by the subroutines of FIG. 12: First, at step S41 the second dispensing block 202 is moved to a location over the reagent placing section 2 and is stopped at a location over a selected reagent rack. Then, at step S42 the tip portion of the reagent pipette 20 is lowered into the selected reagent rack to suck up the reagent.

After the reagent pipette 20 is raised and stopped at step S43, the second dispensing block 202 is moved to a location over the reaction vessel placing section 4 at step 44 and then the reagent pipette 20 is stopped at a location over the reaction vessel 100a into which the specimen has been dispensed. Then, at step S45 the reagent pipette 20 is lowered and the tip portion of the same enters the reaction vessel 100a to dispense the reagent thereinto. After completion of the dispensing of the reagent, the reagent pipette 20 is raised to be on standby for the next operation.

During this process, the specimen pipette 10 is in the cleaning process at step M6. In detail, the cleaning process of the pipette 10 is performed in the order shown by the subroutines of FIG. 13: First, the washing vessel 60 containing a cleaning liquid is positioned in place in the elevating path of the specimen pipette 10 at step S51.

Figure 16:
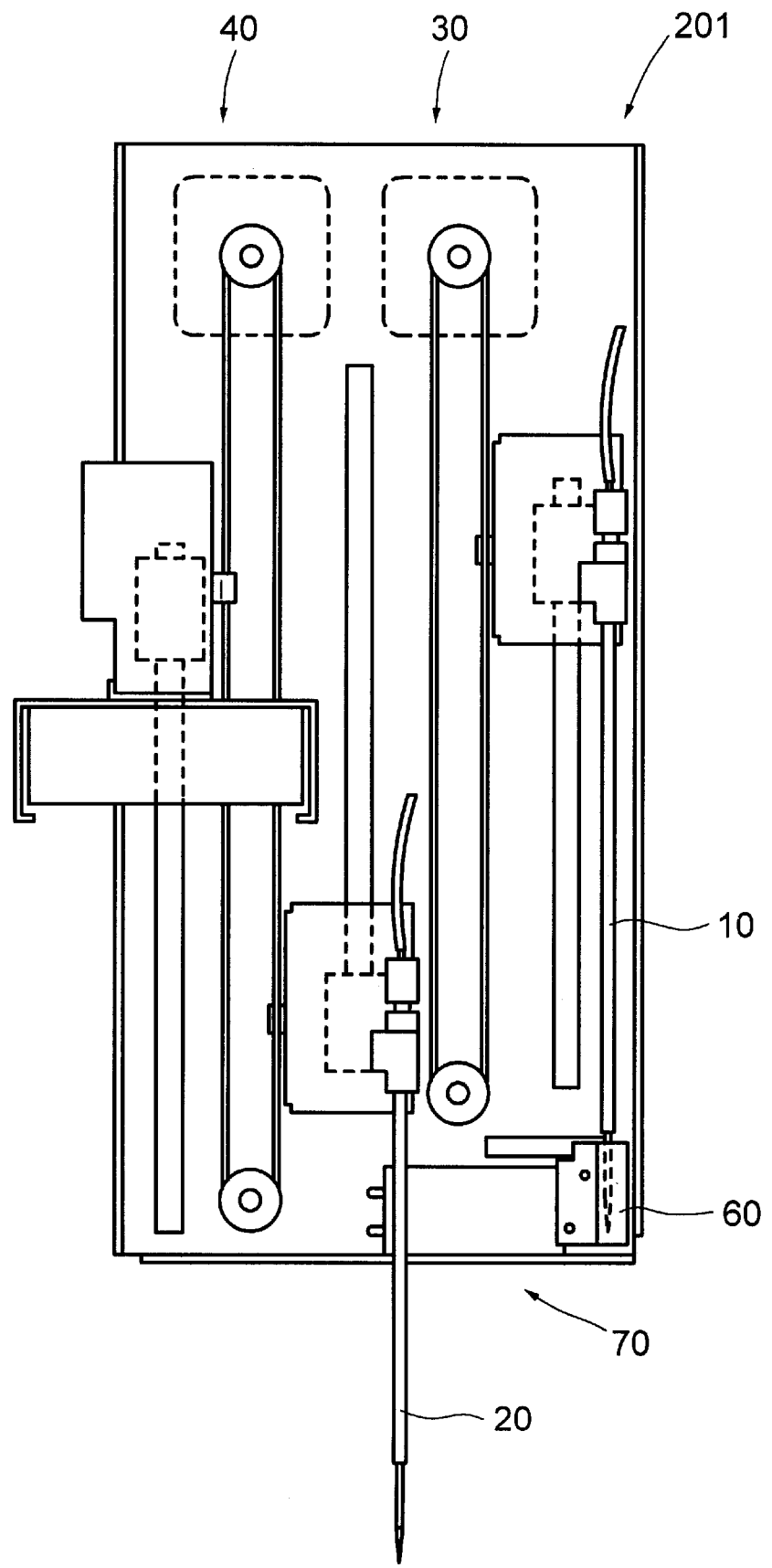
FIG. 16 is a view corresponding to FIG. 2, illustrating the cleaning operation of the specimen pipette and the position of the washing vessel moving means at the time of the dispensing with the specimen pipette.

Then, at step S52 the tip portion of the specimen pipette 10 is lowered into the washing vessel 60 and is stopped at the pipette stopping position, as shown in FIG. 16.

At step S53 the solenoid valve 85 connected to the specimen pipette 10 opens and the cleaning liquid flows into the specimen pipette 10 through the syringe 83 by the drive of the motor 81, so as to clean the interior of the pipette 10. Further, the washing vessel liquid feeding means 90 is driven so that the tip portion of the pipette 10 is immersed in the cleaning liquid for cleaning the exterior of the same.

The cleaning liquid thus supplied is discharged into the reservoir 93 of the washing vessel liquid feeding means 90. After completion of the cleaning, the specimen pipette 10 in the washing vessel 60 is raised by the pipette elevating means 30 at step S54. When the pipette 10 is raised to be on standby for the next operation, the washing vessel 60 located in the elevating path of the specimen pipette 10 is shifted to a place in the elevating path of the reagent pipette 20 by the washing vessel moving means 70.

Then, the dispensing of the reacted solution is made at step M7. In detail, the dispensing of the reacted solution is performed in the order shown by the subroutines of FIG. 14: First, at step S61 the second dispensing block 202 is moved to a location over the reaction vessel placing section 4 and is stopped at a location over the reaction vessel 100a on the reaction plate 100 containing the reacted solution produced by the dispensing of said specimen and said reagent. Then, at step S62 the tip portion of the reacted solution pipette 120 is lowered into the reaction vessel 100a to suck up the reacted solution. If the specimen is of high concentration, it is diluted by sucking up, with the specimen pipette 10, a required amount of diluent liquid which is placed in advance in the reagent placing section 1 and dispensing the diluent liquid into the reaction vessel 100a.

After the reacted solution pipette 120 is raised and stopped at step S63, the second dispensing block 202 is moved to a location over the measurement introducing section 6 at step S64. Then, at step S65 the tip portion of the reacted solution pipette 120 is lowered into the measurement introducing section 6 to dispense the reacted solution thereinto. The reacted solution thus dispensed into the measurement introducing section 6 is measured by a measuring equipment with an optical system (not shown) the data on blood is output to a monitor which is connected to the measuring equipment.

Then, at step S66 the reacted solution pipette 120 is raised and the second dispensing block 202 is moved to a location over the pipette cleaning section 7. Then, at step S67 the reacted solution pipette 120 stopped at a location over the pipette cleaning section 7 is lowered and the tip portion of the same enters the cleaning section 7. Next, the tip portion of the pipette 120 is immersed into a cleaning liquid in a cleaning vessel, (not shown), in the pipette cleaning section 7 so that the exterior of the tip portion of the pipette 120 is cleaned, while the interior of the pipette is cleaned via the drive of a syringe, not shown, connected to the reacted solution pipette 120 and the power source. The wasted cleaning liquid is discharged from the washing vessel by a cleaning liquid fluid feeding means connected to the pipette cleaning section 7. After completion of the cleaning, at step S68 the reacted solution pipette 120 is raised to be on standby for the next operation by the pipette elevating means 30.

Then, at step M8, judgement is made on whether or not the dispensing of the reacted solution into all or selected reaction vessels on the reaction plate 100 is completed and replacement of the reaction place 100 is needed. If the judgement is such that no replacement of the plate 100 is necessary, then the procedure goes to step M3. On the other hand, if the judgement is such that the replacement of the plate 100 is necessary, then the procedure goes to step M9.

At step M9, disposal of the reaction plate 100 is performed. In detail, at this step the first dispensing block 201 is moved to a location over the reaction vessel placing section 4 by the drive of the first block moving means 203, and then the holding means 110 is lowered by the drive of the pipette elevating means 40 to hold the used reaction plate 100. Upon holding the used reaction plate 100, the holding means 110 is raised and is moved to a location over the used vessel placing section 5, and then is lowered to put the used reaction plate 100 on the reaction vessel placing section 5.

Then, at step M10 judgement is made on whether or not a command to stop the dispensing device 210 has been issued. If the judgement is such that the command to stop the dispensing device 210 has been issued, then the dispensing operation is terminated. On the other hand, if the judgement is such that the no command to stop the dispensing device 210 has been issued, then the procedure goes to step M2 to continue the dispensing operation.

In the dispensing device 210 of the above-described embodiment of the invention, since the pipettes 10, 20 disposed in the base 50 are cleaned by use of the washing vessel 60 and the washing vessel moving means 70 provided on the same base 50, the dispensing of the specimen or the reagent, the movement of the base 50, and the cleaning of the pipette 10 or 20 are performed simultaneously. Thus, the respective operation of the dispensing, the movement and the cleaning can be performed continuously with no waiting time involved during the transition from one operation to the next. As a result of this, the dispensing process including the cleaning process can be accelerated for handling a number of specimens with high efficiency.

Advantages of the dispensing device of the invention include the following. With the dispensing device of the invention, a plurality of pipettes situated in the base can be cleaned with the washing vessel and the washing vessel moving means both situated in the same base, so that the cleaning of a pipette can be performed simultaneously with the dispensing action by another pipette or the moving action of the base. Thus, the dispensing of the specimen or the reagent can be continuously carried out without being retarded by the cleaning. This can provide the result that the reciprocating motion of the used pipettes to the washing vessel fixed on the table at each dispensing action, which is required for the conventional dispensing device, can be omitted, thereby substantially saving the time required for each dispensing operation.

Where the washing vessel moving means is in the form of an actuator which, when one of the pipettes is in its lower position, allows the washing vessel to be positioned in place in the elevating path of the other pipette which is in its upper position, and, when the other pipette is in its lower position, allows the washing vessel to be positioned in place in the elevating path of the one pipette which is in its upper position, it can be ensured that each pipette is not hindered from its lowering motion by the washing vessel when it is lowered to the dispensing position. Consequently, the shifting operation of the washing vessel and the elevating operation of the two pipettes can be controllably associated with each other with ease.

Where the washing vessel is connected to a washing vessel cleaning means for introducing a cleaning liquid in and out of the washing vessel, and the pipettes are connected to a fluid feeding means for supplying a cleaning liquid into the pipettes, both the exterior and interior of each pipette can be cleaned in the washing vessel in a very short time.

Further, where the base moving means is capable of being linked, in operation, with at least one of the washing vessel moving means, the pipette elevating means, the washing vessel cleaning means, and the fluid feeding means, that can provide the result that at least part of the cleaning process can be performed simultaneously while one of the pipettes held on the base is moved. Accordingly, the time required for each dispensing operation can be substantially saved.

Additionally, where the washing vessel moving means comprises a rotary actuator mounted on the base and having a vertical rotary axis and an arm having one end supported by the vertical rotary axis and the other end supporting the washing vessel, that can provide the result that the arm is simply required to swing or pivot around the vertical rotary axis of the rotary actuator to move between the two places. Therefore, a facilitated control of the washing vessel moving means can be provided and also simplification of the device can be achieved.

Also, where the dispensing device further comprises a vessel sensing means for sensing the washing vessel positioned in place in either of the elevating paths of the pipettes, it can be ensured that in the pipettes are prevented from being damaged and also the tip portions of the pipettes are introduced into the washing vessel.

Thus, the invention can provide a dispensing device capable of enhancing efficiencies of the dispensing operations including the cleaning operations for handling a number of specimens efficiently.

What is claimed is:

1. A dispensing device comprising:
   at least two dispensing pipettes for sucking and discharging liquid;
   a pipette elevating means for holding the pipettes and selectively raising and lowering each pipette along an elevating path thereof;
   a washing vessel in which each pipette is alternately immersed to be cleaned;
   a washing vessel moving means for holding the washing vessel and allowing the washing vessel to selectively move between locations in the elevating paths of the pipettes;
   a base for holding the washing vessel moving means for washing vessel movement between the elevating path locations and for holding the pipette elevating means for movement of each pipette into the washing vessel when the washing vessel is in the pipette's elevating path; and
   a base moving means for moving the base;
   whereby one pipette can be cleaned simultaneously with a discharging or a sucking action of the other pipette or a moving action of the base.

2. The dispensing device according to claim 1, wherein the washing vessel moving means is in the form of an actuator which, when a first pipette is in its lower position, allows the washing vessel to be positioned in place in the elevating path of a second pipette which is in its upper position, and, when the second pipette is in its lower position, allows the washing vessel to be positioned in place in the elevating path of the first pipette which is in its upper position.

3. The dispensing device according to claim 1 or 2, wherein the first pipette is a specimen pipette for use in dispensing a specimen and the second pipette is a reagent pipette for use in dispensing a reagent.

4. The dispensing device according to claim 1, wherein the washing vessel is connected to a washing vessel cleaning means for introducing a cleaning liquid in and out of the washing vessel, and the pipettes are connected to a fluid feeding means for supplying a cleaning liquid into the pipettes.

5. The dispensing device according to claim 4, wherein the base moving means is capable of interlocking in operation with at least one of the washing vessel moving means, the pipette elevating means, the washing vessel cleaning means, and the fluid feeding means.

6. The dispensing device according to claim 1, wherein the washing vessel moving means comprises a rotary actuator mounted on the base and having a vertical rotary axis and an arm having one end supported by the vertical rotary axis and the other end supporting the washing vessel.

7. The dispensing device according to claim 1 or 2, further comprising a vessel sensing means for sensing the washing vessel positioned in place in one of the elevating paths of the pipettes.

8. The dispensing device according to claim 7, wherein the vessel sensing means comprises a magnet fixed to the arm and Hall effect devices which are located in such places in the pipette elevating paths as to be linked in operation with the magnet.

9. The dispensing device according to claim 1, wherein the pipette elevating means comprises a pair of upper and lower horizontal axes mounted on the base; a belt stretched between the horizontal axes; a pipette moving element clamped to the belt for allowing the pipette to be held vertically; and a belt driving motor for driving the belt mounted on the base, wherein the base moving means comprises a threaded shaft including a horizontal shaft, a base moving element threadedly engaged with the threaded shaft and supporting the base, and a threaded shaft driving motor for rotating the threaded shaft.

10. The dispensing device according to claim 4, wherein the washing vessel cleaning means comprises a liquid feeding path connected to a lower part of the washing vessel, a liquid discharging path connected to an upper part of the washing vessel, and a washing vessel pump which is connected to the liquid feeding path so that the cleaning liquid can be fed from the lower part of the washing vessel and discharged from the upper part of the washing vessel through the liquid discharging path, wherein the fluid feeding means comprises a quantifying syringe connected to an upper end portion of the pipette and a pipette pump capable of feeding the cleaning liquid to the quantifying syringe.

11. An immunoassay apparatus comprising a table on which specimens including blood, reagents, and reaction vessels are placed; an immunoassay section; a specimen/reagent dispensing section disposed above the table for dispensing the specimen and the reagent into the reaction vessels; and a reacted solution dispensing section for dispensing reacted solutions from the reaction vessels to said measuring section, wherein said specimen/reagent dispensing section is formed by the dispensing device according to claim 1.

* * * * *